United States Patent
Linares

(10) Patent No.: US 8,343,225 B2
(45) Date of Patent: Jan. 1, 2013

(54) SKULL PATCH WITH DURABLE PLASTIC CONSTRUCTION AND UNDERCUT MOUNT TO EXISTING SKULL PERIMETER

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 254 days.

(21) Appl. No.: 12/788,370

(22) Filed: May 27, 2010

(65) Prior Publication Data

US 2010/0312284 A1   Dec. 9, 2010

Related U.S. Application Data

(60) Provisional application No. 61/184,361, filed on Jun. 5, 2009.

(51) Int. Cl.
*A61B 17/80* (2006.01)

(52) U.S. Cl. ............... 623/17.19; 606/286; 606/298

(58) Field of Classification Search ............ 606/70–71, 606/280–291, 295–298, 902–903, 76, 77, 606/331; 623/17.19
See application file for complete search history.

(56) References Cited

U.S. PATENT DOCUMENTS

| | | | |
|---|---|---|---|
| 4,328,813 A | 5/1982 | Ray | |
| 5,108,435 A * | 4/1992 | Gustavson et al. | 623/23.53 |
| 5,201,737 A | 4/1993 | Leibinger et al. | |
| 5,468,242 A | 11/1995 | Reisberg | |
| 5,545,226 A * | 8/1996 | Wingo et al. | 623/17.19 |
| 5,702,396 A | 12/1997 | Hoenig et al. | |
| 5,752,958 A | 5/1998 | Wellisz | |
| 6,350,284 B1 * | 2/2002 | Tormala et al. | 623/17.19 |
| 6,544,266 B1 * | 4/2003 | Roger et al. | 606/70 |
| 6,572,623 B1 | 6/2003 | Birchall, Jr. et al. | |
| 6,685,707 B2 | 2/2004 | Roman et al. | |
| 7,004,948 B1 | 2/2006 | Pianca et al. | |
| 7,198,046 B1 | 4/2007 | Argenta et al. | |
| 7,216,651 B2 | 5/2007 | Argenta et al. | |
| 7,479,146 B2 | 1/2009 | Malinowski | |
| 7,520,872 B2 | 4/2009 | Biggie et al. | |
| 2004/0034356 A1 | 2/2004 | LeHuec et al. | |
| 2004/0243145 A1 | 12/2004 | Bobo et al. | |
| 2006/0224242 A1 * | 10/2006 | Swords et al. | 623/17.19 |
| 2007/0083268 A1 * | 4/2007 | Teoh et al. | 623/17.19 |
| 2008/0051786 A1 * | 2/2008 | Jensen | 606/61 |
| 2008/0154310 A1 | 6/2008 | White et al. | |

* cited by examiner

*Primary Examiner* — Kevin T Truong
*Assistant Examiner* — Christian Sevilla
(74) *Attorney, Agent, or Firm* — Gifford, Krass, Sprinkle, Anderson & Citkowski, P.C.

(57) ABSTRACT

A patch for covering an aperture associated with a skull including a plastic composite body having either a planar or arcuate shape exhibits an extending edge profile which matches a profile associated with a reconditioned edge of the skull. A fastener extends through the edge profile for securing the body to the skull. The extending edge profile further includes a first portion and a second reduced portion separated by a shoulder, the skull exhibiting a corresponding outer skull edge portion, inner stepped skull portion and intermediate shoulder being configured to mate with the configuration of the extending edge profile and in order to achieve a generally flush appearance when seating the patch over the skull aperture. One or more screws fasten the edge profile of the body to the skull. This can further include a bone screw with undercut engaging portion extending through the extending edge profile and associated skull location.

5 Claims, 3 Drawing Sheets

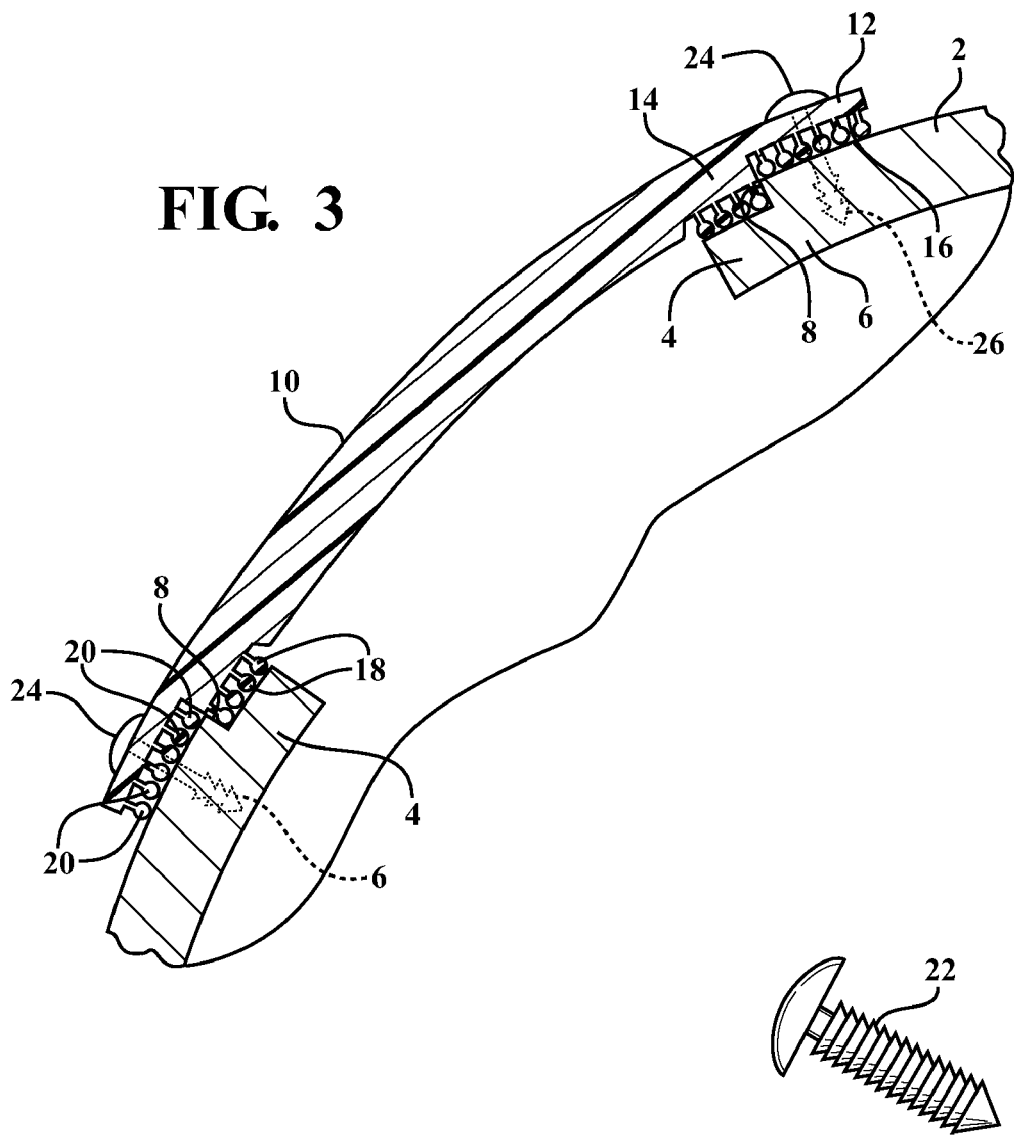
FIG. 3
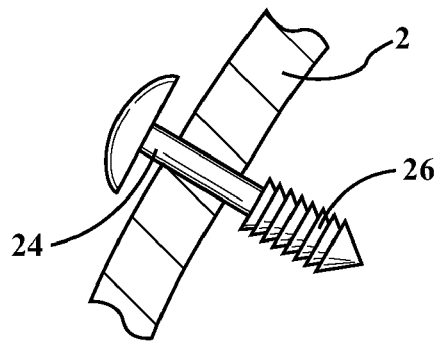
FIG. 3A
FIG. 3B

SKULL PATCH WITH DURABLE PLASTIC CONSTRUCTION AND UNDERCUT MOUNT TO EXISTING SKULL PERIMETER

CROSS-REFERENCE TO RELATED APPLICATIONS

This Application claims the benefit of U.S. Provisional Application 61/184,361 filed on Jun. 5, 2009.

FIELD OF THE INVENTION

The present invention discloses a composite plasticized patch for covering a hole in a patient's skull, such as resulting from bone disease, traumatic injury or the like. More particularly, the skull patch includes a stepped extending edge profile which is configured with undercut and bone marrow growth promoting portions. The patch is constructed of a plastic or related composite and is dimensioned so as to establish a seating engagement with a pre-conditioned inner facing edge profile of the skull defining a boundary of the hole

BACKGROUND OF THE INVENTION

The incidence of skull fractures resulting in loss of bone is known in the prior art. A challenge of medically treating such conditions is in finding a suitable patch or covering for fashioning about a perimeter edge resulting from loss of skull portion, such as further resulting from disease or traumatic injury.

SUMMARY OF THE INVENTION

The present invention discloses a patch for covering an aperture associated with a skull and including a plastic composite body having either a planar or arcuate shape exhibiting an extending edge profile which matches a profile associated with a reconditioned edge of the skull. A fastener extends through the edge profile for securing the body to the skull.

The extending edge profile further includes a first portion and a second reduced portion separated by a shoulder, the skull exhibiting a corresponding outer skull edge portion which is fashioned using such as a medical drill. Both the inner stepped skull portion and intermediate shoulder mate with the configuration of the extending edge profile in order to establish a generally flush appearance when mounting the patch over the prepared skull perimeter edge profile.

One or more screws fasten the edge profile of the body to the skull. This can further include a bone screw with undercut engaging portion extending through the extending edge profile and associated skull location.

BRIEF DESCRIPTION OF THE DRAWINGS

Reference will now be made to the attached drawings, when read in combination with the following detailed description, wherein like reference numerals refer to like parts throughout the several views, and in which:

FIG. 3 is an enlarged and cutaway illustration, similar to that shown in FIG. 1, and illustrating the mating stepped profile established between the outer perimeter of the patch and the corresponding inner perimeter of the skull;

FIG. 3A is a subset illustration of a bone screw utilized in the patch to skull engagement of FIG. 3;

FIG. 3B is a further subset illustration showing an alternately configured bone screw with undercut engaging portion which extends through an edge of the patch and an associated skull location;

DETAILED DESCRIPTION OF THE PREFERRED EMBODIMENTS

Figure 1:
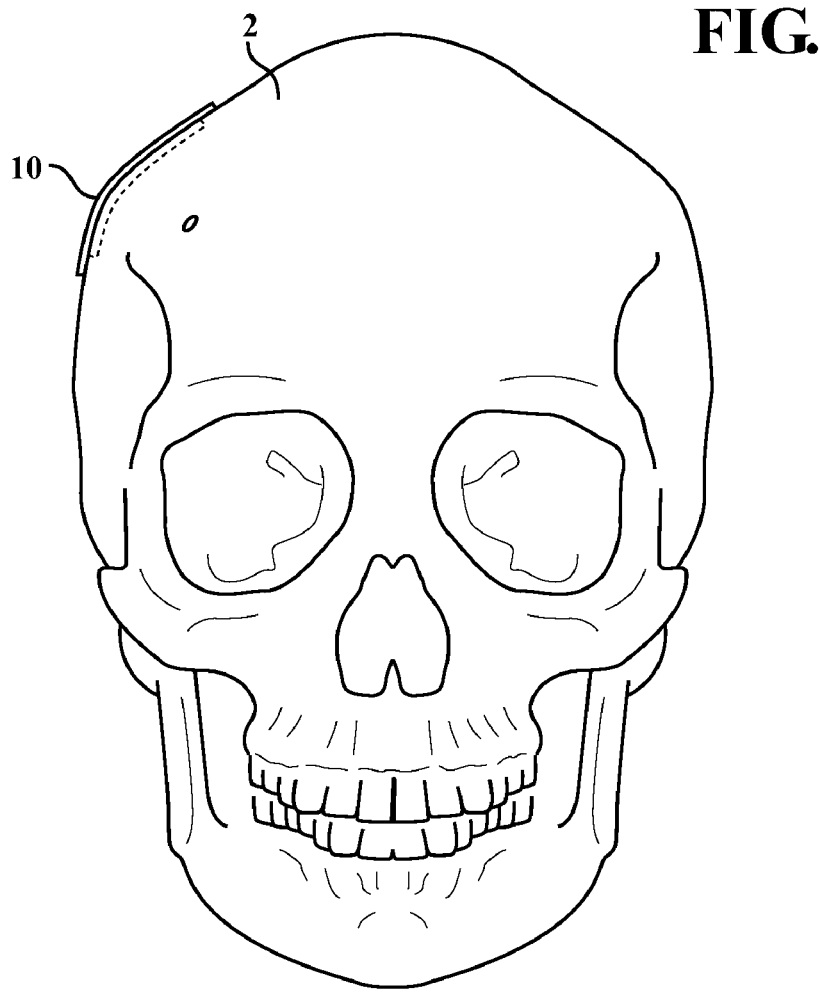
FIG. 1 is a plan view illustration of a patch installed upon a previously conditioned edge profile associated with a human skull according to the present invention.

Referring now to the several illustrations, FIG. 1 is a plan view illustration of a patch 10 installed upon a previously conditioned edge profile associated with a human skull 2 according to the present invention. As previously described, the present invention discloses a composite plasticized patch for covering a hole in a patient's skull, such as resulting from bone disease, traumatic injury or the like.

More particularly, and as will be further described in detail with reference to succeeding illustrations FIGS. 2A, 2B and 3, the skull patch includes a stepped extending edge profile which is configured with undercut and bone marrow growth promoting portions. The patch 10 is constructed of a plastic or related composite, such as which can be further treated with anti-microbial materials.

The patch 10 is further dimensioned to include a main body thickness (associated with main body 10) and a reduced thickness dimension edge section 12 so as to establish a seating engagement with a pre-conditioned inner facing edge profile of the skull (see as further described in FIG. 3) defining a boundary of the hole in the skull.

Figure 4:
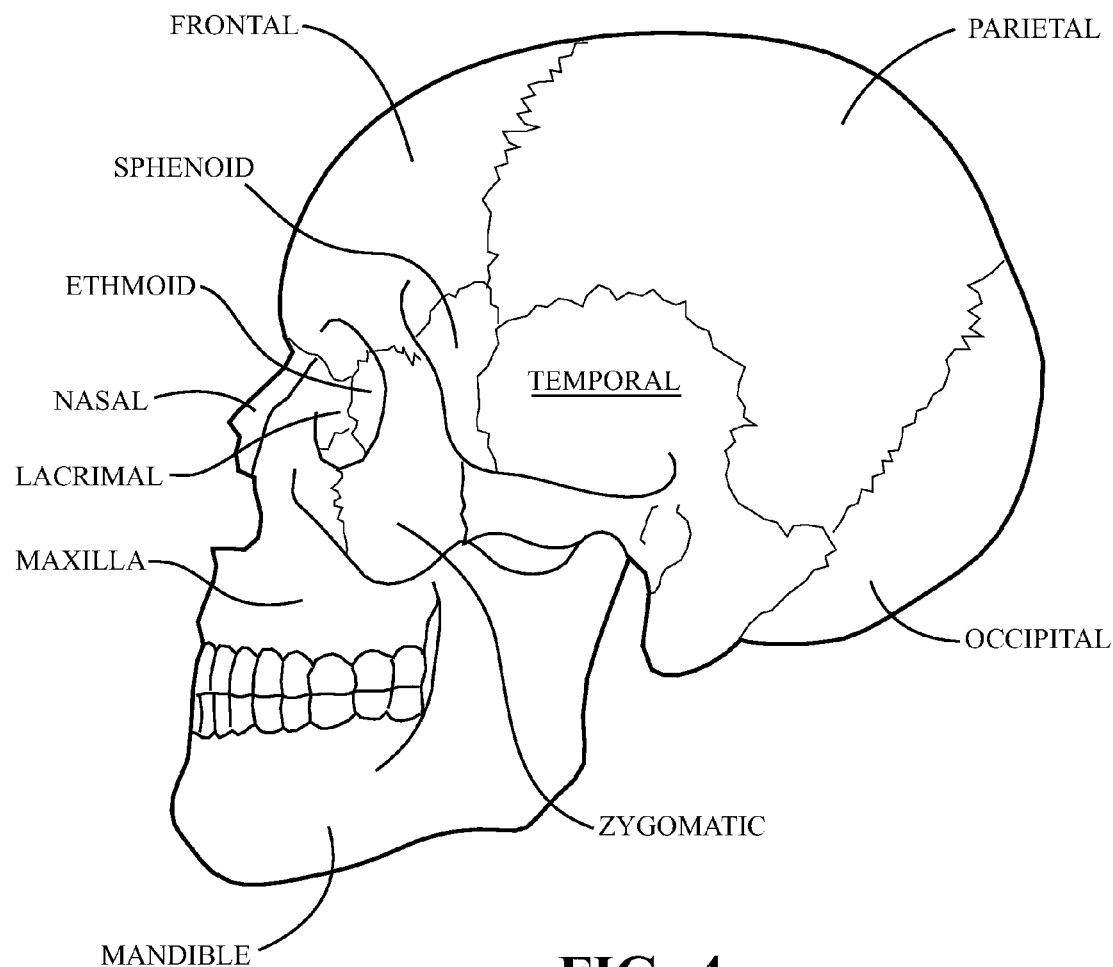
FIG. 4 is a Prior Art illustration of the human skull and representing the various bones with which the skull patch of the present invention is utilized.

As shown in the prior art view of FIG. 4, the adult skull is normally made up of twenty two bones. Except for the mandible (jaw bone), all of the bones of the skull are joined together by sutures or rigid articulations permitting very little movement. A subset of eight bones form the neurocranium (or braincase) and include the frontal, parietals, occipital bone, sphenoid, temporals and ethmoid, these collectively defining protective vault surrounding the brain. The fourteen remaining bones form the splanchnocranium supporting the face.

As is also known, a damaged area of the skull can result from such as a degenerative bone disease, traumatic injury or the like. Although applicable to most bones associated with the skull, this is particularly the applicable to the larger braincase defined bones including namely again the frontal, parietal, temporal and occipital lobes.

Figure 2A:
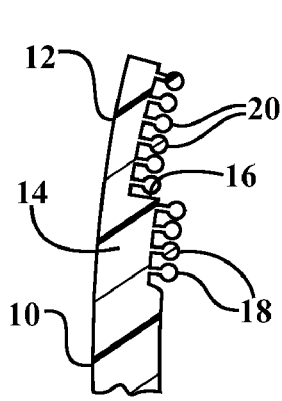
FIG. 2A is a partial illustration of an edge section associated with the skull patch.

Referring now to FIG. 2A is a partial illustration of an edge section 12 associated with the skull patch 10. The patch 10 includes a generally flattened or curved body again constructed of either a plastic or plastic composite material (such as further contemplating the incorporation of metal, ceramic or other particulate materials). The perimeter extending edge section 12 is shown in side profile and further exhibits an underside including a first edge proximate portion 14 (corresponding in thickness to the main body of the patch) in communication with the second reduced thickness edge section 12 separated by an intermediate step 16.

Figure 2B:
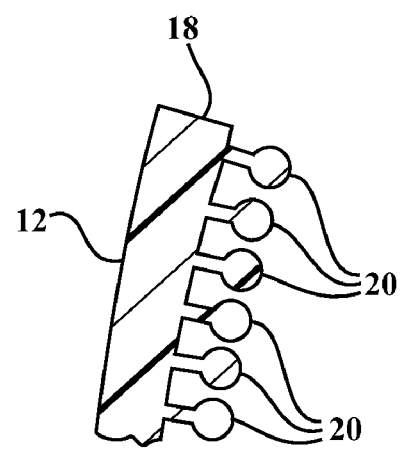
FIG. 2B is an enlarged subset illustration of the edge section shown in FIG. 2A and further showing the undercut and bone marrow growth promoting portions which are defined between a stepped shoulder associated with the edge profile of the patch.

As further shown in the enlarged subset illustration of FIG. 2B, pluralities of undercut and bone marrow growth promoting portions 18 and 20 are defined along the underside facing edges of the patch corresponding to first edge proximate portion 14 and outer most reduced thickness edge portion 12 along its perimeter. The undercut growth promoting portions 18 and 20 each exhibit any desired configuration, such as exhibiting enlarged and stem displaced ends, and cover either or both the underside stepped portions on both sides of the intervening shoulder 16. Beyond that shown, the underside facing portions 18 and 20 can exhibit any other desired shape or configuration and which promotes bonding with natural bone growth associated with the previously conditioned and aperture defining edges of the skull bone.

FIG. 3 is an enlarged and cutaway illustration, similar to that shown in FIG. 1, and illustrating the mating stepped profile established between the outer perimeter of the patch and a corresponding inner perimeter edge defined in the skull 2. This includes a corresponding stepped edge with first outer skull edge portion 4, a second inner upwardly stepped (increased dimension) skull portion 6 separated an intermediate shoulder 8, these mating with the configuration of the outer reduced dimension edge 12, inner proximate increased dimension portion 14 and separating shoulder 16 in order to establish smooth and relatively flush seating engagement of the patch 10 within the previously conditioned location of the skull 2. As previously described, a suitable medical drill (not shown) can be provided in order to create the desired and conditioned edge profile (such as to a previously damaged fracture or disease location) and prior to matching with an appropriately sized rigid composite plastic patch 10.

In use, the eventual dimension of the skull aperture (again in 2D profile in FIG. 3) is determined following a pre-conditioning process by which a damaged area of the bone is removed and the remaining edge is smoothed and reconditioned through the application of an appropriate medical drill and/or routing tool. At this point, the dimensions established by the resulting skull edge stepped profile are factored into the creation of the desired patch 10, and such as which can be accomplished by a molding, extrusion or suitable stamping operation. For larger sized patches, a mold template of some type may be desirous to impart a desired three dimensional shape to more accurately mimic the contour of the damaged and previously removed skull bone.

At this point, and upon applying the patch 10 over the conditioned perimeter bone edge, the undercut marrow growth promoting portions 18 and 20 of the patch 10 initiate bonding with the contacting stepped surfaces 4 and 6 of the bone edge. It is further envisioned that understood that the conditioned edge surfaces 4 and 6 of the skull bone can exhibit any type of surface roughening and/or the formation of holes or apertures in order to further facilitate seating and bonding with the undercut growth promoting portion 18 and 20, thus serving both to increase the bond line strength established between the bone 2 and patch 10, as well as to promote more even alignment and seating of the patch within the conditioned bone aperture interface.

FIG. 3A is a subset illustration of a bone screw 22 according to one possible design and which can be utilized in the patch to skull engagement of FIG. 3. Finally, FIG. 3B is a further subset illustration showing an alternately configured bone screw 24 with undercut engaging portion 26 which extends through an edge location of the patch and associated skull location in order to fixedly secure the patch in place (see FIG. 3), such as during an intervening time interval in which natural bone growth occurs in order to permanently fuse the patch in location over the reconditioned skull aperture.

Having described my invention, other and additional preferred embodiments will become apparent to those skilled in the art to which it pertains, and without deviating from the scope of the appended claims.

I claim:

1. A patch kit for covering a perimeter edge conditioned aperture associated with a skull, said kit comprising:
   a plasticized body exhibiting an outer perimeter extending edge profile which matches an inner extending profile associated with a reconditioned edge of the skull;
   said extending edge profile further comprising a first edge proximate portion and a second outermost and reduced thickness portion separated by a shoulder so as to define an underside stepped configuration, the inner perimeter extending edge profile of the skull exhibiting a corresponding outer skull edge portion, an inner stepped skull portion and an intermediate shoulder defining a mating stepped configuration such that the skull edge profile is adapted to mate with said extending edge profile of said patch;
   a fastener extending through said edge profile for securing said body to the skull;
   pluralities of undercut growth promoting portions extending from said first and second portions associated with said underside stepped configuration and which, upon mating with the stepped skull profile, serving to increase a bond line strength established between the bone and patch as well as to promote more even alignment and seating of the patch within the reconditioned and inner extending skull profile; and
   said undercut growth promoting portions further comprising spherical shaped portions mounted to narrowed stem supporting portions extending from underside locations of said first and second portions.

2. The patch kit as described in claim 1, said body being constructed of at least one of a plastic and a composite plastic material.

3. The patch kit as described in claim 1, said body exhibiting at least one of a planar and an arcuate shape.

4. The patch kit as described in claim 1, said fastener further comprising a screw.

5. The patch kit as described in claim 1, said fastener further comprising a bone screw having undercut engaging portion extending through said extending edge profile and associated skull location.

* * * * *